United States Patent
Ridler et al.

(10) Patent No.: US 11,338,147 B2
(45) Date of Patent: *May 24, 2022

(54) SHIELDING DEVICE FOR SIGNAL TRANSMISSION COIL

(71) Applicant: Cochlear Limited, Macquarie University (AU)

(72) Inventors: Oliver John Ridler, Macquarie University (AU); Adam Mujaj, Macquarie University (AU); Thomas Cooney, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 75 days.

This patent is subject to a terminal disclaimer.

(21) Appl. No.: 16/871,690

(22) Filed: May 11, 2020

(65) Prior Publication Data

US 2020/0330776 A1    Oct. 22, 2020

Related U.S. Application Data

(63) Continuation of application No. 14/807,473, filed on Jul. 23, 2015, now Pat. No. 10,843,000.

(60) Provisional application No. 62/028,133, filed on Jul. 23, 2014.

(51) Int. Cl.
| | | |
|---|---|---|
| *A61N 1/372* | (2006.01) | |
| *A61N 1/05* | (2006.01) | |
| *A61N 1/36* | (2006.01) | |
| *A61N 1/378* | (2006.01) | |

(52) U.S. Cl.
CPC ....... *A61N 1/37229* (2013.01); *A61N 1/0541* (2013.01); *A61N 1/36036* (2017.08); *A61N 1/3787* (2013.01); *A61N 1/36038* (2017.08)

(58) Field of Classification Search
CPC ............ A61N 1/37229; A61N 1/36036; A61N 1/0541; A61N 1/3787; A61N 1/36038
See application file for complete search history.

(56) References Cited

U.S. PATENT DOCUMENTS

| | | |
|---|---|---|
| 2009/0240099 A1 | 9/2009 | Conn |
| 2010/0046778 A1 | 2/2010 | Crawford et al. |
| 2011/0224789 A1 | 9/2011 | Griffith |
| 2011/0257703 A1 | 10/2011 | Kerber et al. |
| 2015/0025613 A1 | 1/2015 | Nyberg, II et al. |

FOREIGN PATENT DOCUMENTS

| | | |
|---|---|---|
| KR | 20080055571 A | 6/2008 |
| KR | 20100005940 A | 1/2010 |
| KR | 101297828 B1 | 8/2013 |

*Primary Examiner* — Paula J Stice
(74) *Attorney, Agent, or Firm* — Edell, Shapiro & Finnan, LLC

(57) ABSTRACT

Systems and apparatuses are used to transmit data between external and internal portions of auditory prostheses or other medical devices. The external portion of the auditory prosthesis includes a magnet and an implanted coil that provides stimulation to the device recipient. A shaped shield material can be placed between the external coil and the sound processing hardware to improve efficiency and effectiveness between the external coil and implanted coil. Adverse effects on tuning frequencies can be reduced by disposing the shield material away from the magnet.

20 Claims, 7 Drawing Sheets

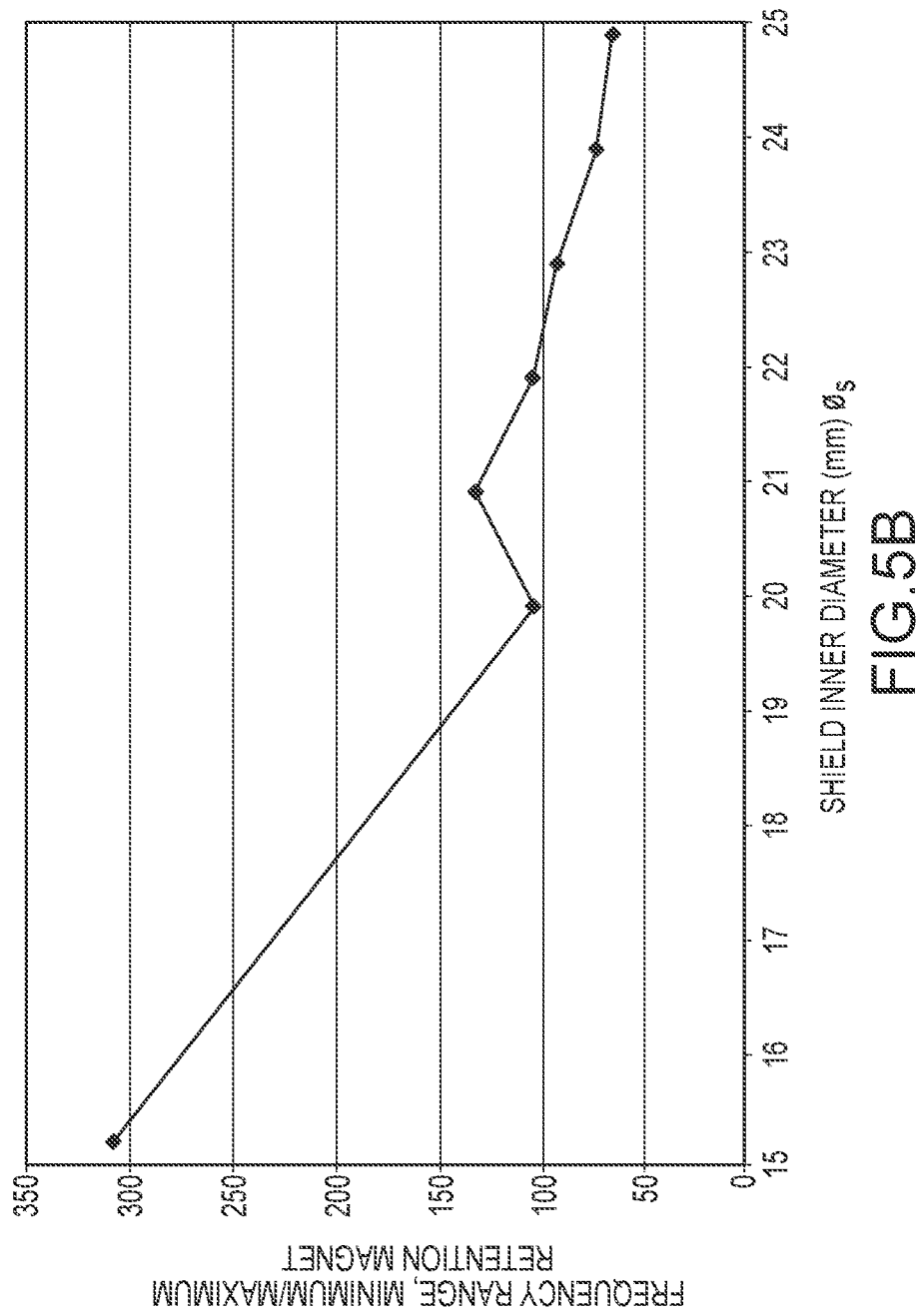

SHIELDING DEVICE FOR SIGNAL TRANSMISSION COIL

CROSS-REFERENCE TO RELATED APPLICATIONS

This application is a continuation of U.S. patent application Ser. No. 14/807,473, filed Jul. 23, 2015, now U.S. Pat. No. 10,843,000, entitled, "SHIELDING DEVICE FOR SIGNAL TRANSMISSION COIL", which claims the benefit of U.S. Provisional Patent Application No. 62/028,133, filed Jul. 23, 2014, entitled, "SHIELDING DEVICE FOR SIGNAL TRANSMISSION COIL." The disclosure of these priority applications are hereby incorporated by reference in their entirety into the present application.

BACKGROUND

Auditory prostheses, such as cochlear implants, include an implantable portion having a stimulating assembly with an implanted coil and an external portion having a coil, speech processing hardware and software, as well as a battery. Magnets are also disposed in both portions to hold the external portion proximate the implanted portion. A shield of ferrite or other magnetic material is installed between the external coil and the speech processing hardware to improve radio frequency (RF) link efficiency and effectiveness with the implanted coil. This shield, however, can make the coil-tuned frequency unacceptably sensitive to the magnetic flux from the external magnet.

SUMMARY

Embodiments disclosed herein relate to systems and apparatuses that are used to transmit data between external and internal portions of medical devices. Those devices include, for example, cochlear implants or other auditory prostheses or devices. The external portion of the auditory prosthesis includes a magnet and is powered by an on-board battery and sends signals via a coil. An implanted coil receives the signals and provides stimulation to the device recipient. A shaped shield material can be placed between the external coil and the sound processing hardware to improve efficiency and effectiveness with the implanted coil, and minimize adverse effects caused by the magnet.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

FIG. 5B depicts results from a test of frequency ranges based on an inner shield diameter, in an auditory prosthesis.

DETAILED DESCRIPTION

Figure 1:
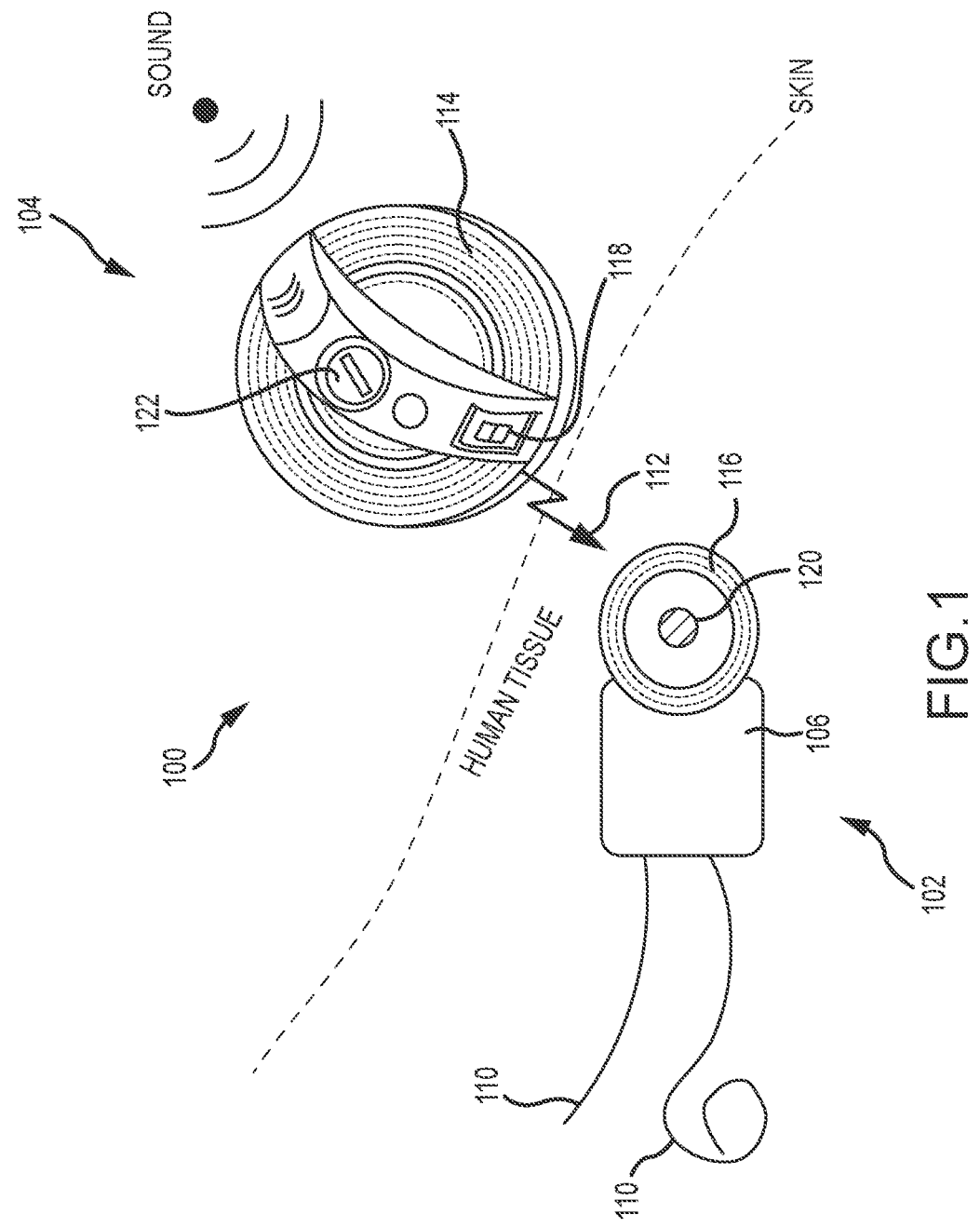
FIG. 1 is a perspective view of an auditory prosthesis, including an implantable portion and an external portion.

While the technologies disclosed herein have particular application in the cochlear implant devices depicted in FIG. 1, it will be appreciated that the systems, methods, and apparatuses disclosed can be employed in other types of hearing prostheses. For example, the technologies disclosed can be utilized in devices such as active transcutaneous bone conduction devices, passive transcutaneous devices, middle ear implants, or other devices that include an external coil and an internal or implanted coil. Furthermore, the embodiments disclosed herein can be utilized to transmit signals to medical devices other than hearing prostheses. The technologies disclosed herein will be described generally in the context of external portions of medical devices where the external portions utilize a coil for transmission of data and/or other signals. Such signals can also include signals sent by a charging coil that charges a totally-implantable cochlear implant or other medical device. For clarity, however, the aspects disclosed herein will be described in the context of cochlear implant auditory prostheses and, more specifically, the external portions and coils used therewith.

FIG. 1 is a perspective view of an auditory prosthesis 100, in this case, a cochlear implant, including an implantable portion 102 and an external portion 104. The implantable portion 102 of the cochlear implant includes a stimulating assembly 106 implanted in a body (specifically, proximate and within the cochlea) to deliver electrical stimulation signals to the auditory nerve cells, thereby bypassing absent or defective hair cells. The electrodes 110 of the stimulating assembly 106 differentially activate auditory neurons that normally encode differential pitches of sound. This stimulating assembly 106 enables the brain to perceive a hearing sensation resembling the natural hearing sensation normally delivered to the auditory nerve.

The external portion 104 includes a speech processor that detects external sound and converts the detected sound into a coded signal 112 through a suitable speech processing strategy. The coded signal 112 is sent to the implanted stimulating assembly 106 via a transcutaneous link. The signal 112 is sent from an external coil 114 located on the external portion 104 to an implantable coil 116 on the implantable portion 102, via a radio frequency (RF) link. The signal 112 can be data, power, audio, or other types of signals, or combinations thereof. Coils 114, 116 can be circular, substantially circular, oval, substantially oval, D-shaped or have other shapes or configurations. The efficiency of power transfer and integrity of the data transmission from one coil to the other is affected by the coil coupling coefficient (k). Coil coupling coefficient k is a unitless value that indicates the amount of the shared magnetic flux between a first coil and a second, coupled (associated) coil. As the amount of shared magnetic flux decreases (i.e., as the coil coupling coefficient k decreases), efficient power transfer between the two coils becomes increasingly difficult. Therefore it is advantageous to maximize the coil coupling coefficient k in a system where power and/or data are transferred between two coils. The stimulating assembly 106 processes the coded signal 112 to generate a series of stimulation sequences which are then applied directly to the auditory nerve via the electrodes 110 positioned within the cochlea. The external portion 104 also includes a battery and a status indicator 118. Permanent magnets 120, 122 are located on the implantable portion 102 and the external portion 104, respectively. In the depicted device, the external portion 104 includes a microphone port connected to a microphone that receives sound. The microphone is connected to one or more internal processors that process and convert the sound into stimulation signals that are sent to the implantable portion 102.

Figure 2:
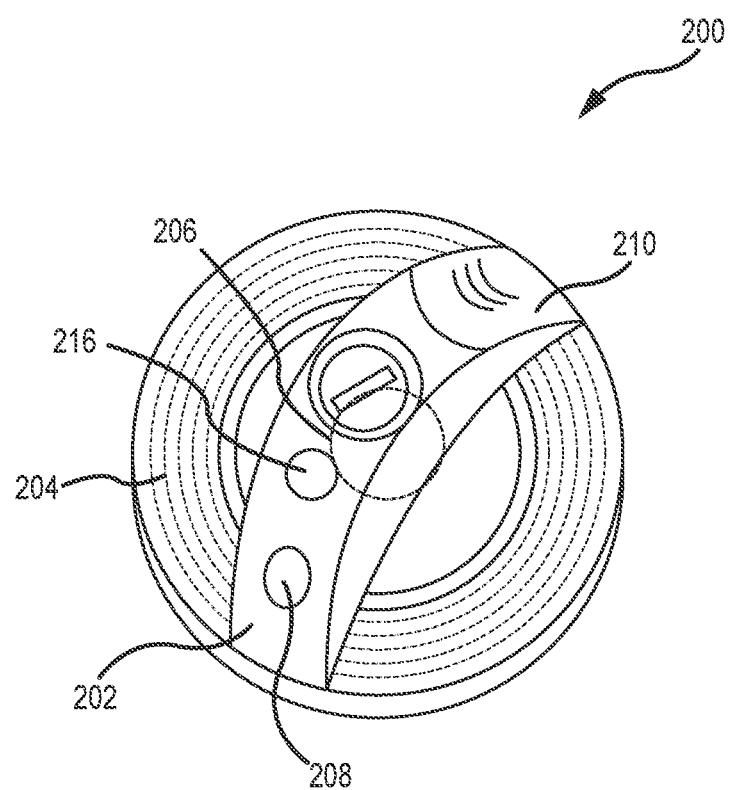
FIG. 2 is a perspective view of an external portion of an auditory prosthesis.

FIG. 2 is a perspective view of an external portion 200 of an auditory prosthesis. The external portion 200 includes a body 202. For context, approximate locations of various elements disposed in the body 202 are depicted, although those elements would not necessary be visible from the outside of the body 202. More detailed figures depicting the various elements are depicted below. An external coil 204 is disposed in the body 202, as is a permanent magnet 206, as described above. The external portion 200 can include an indicator 208 such as a light emitting diode (LED). A battery door 210 covers a receptacle that includes a battery that provides internal power to the various components of the external portion 200 and the implantable portion.

It is desirable that auditory prostheses maintain a high coil quality factor (Q). Coil quality factor Q is a unitless value that indicates the how much energy is lost relative to the energy stored in the resonant circuit that includes the coil. A higher coil quality factor Q indicates a lower rate of energy loss relative to the stored energy of the resonant circuit. Coil quality factor Q can be calculated for an ideal series RLC circuit as depicted in Equation I:

$$Q = \frac{1}{R}\sqrt{\frac{L}{C}} = \frac{\omega_0 L}{R}$$

Here, L is the measured inductance of the coil, R is the measured resistance of the coil, and $\omega_0 = 2 \times Pi \times Frequency$. As the coil quality factor Q decreases, it becomes increasingly difficult to transfer power efficiently from one coil to an associated coil. Therefore, it is advantageous to maximize the coil quality factor Q in a system where power is transferred between two coils.

A high coil quality factor Q is desirable, even while the electronics and batteries are in close proximity to the coil, as depicted in FIG. 2. Placing metallic components, e.g., a battery, above the coil 204, as depicted in FIG. 2, can have an adverse effect on coil Q. A reduced coil Q, however, results in a lower efficiency RF link, which ultimately results in a shorter battery life. To address this in the configuration depicted in FIG. 2, a shield material such as a ferrite, ferrimagnetic, or ferromagnetic material can be disposed above the coil 204. Any other material that substantially redirects the magnetic flux generated by the coil 204 can also be utilized. Materials that redirect magnetic flux can, in certain embodiments, be defined by a high magnetic flux permeability. This can help alleviate the adverse effect on coil Q, but adds weight and size to the device, which is also undesirable, since the external portion 200 is worn on the head of a recipient. It also adversely affects the tuning frequency of the coil. Configuration and placement of the shield material to address issues related to weight, tuning frequency, etc., is described in more detail below. In addition to external coil quality factor Q, the relationship between the tuned frequency of the external coil and implantable coil has a significant impact on the efficiency and effectiveness of the RF link. The tuned frequency of the external coil and implantable coil are selected to balance the needs of RF data integrity and power transfer. Any significant deviation from these selected tuned frequencies can reduce the efficiency and effectiveness of the RF link.

Figure 3:
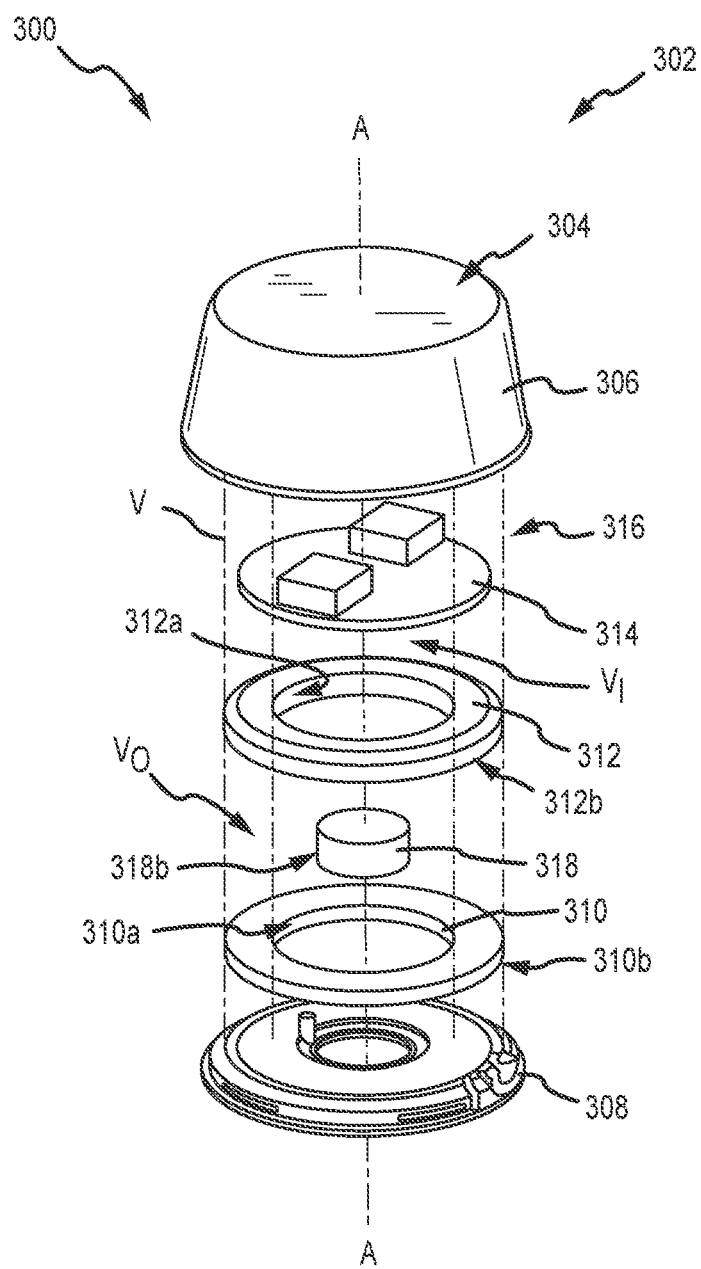
FIG. 3 is an exploded perspective view of an external portion of an auditory prosthesis.
Figure 4:
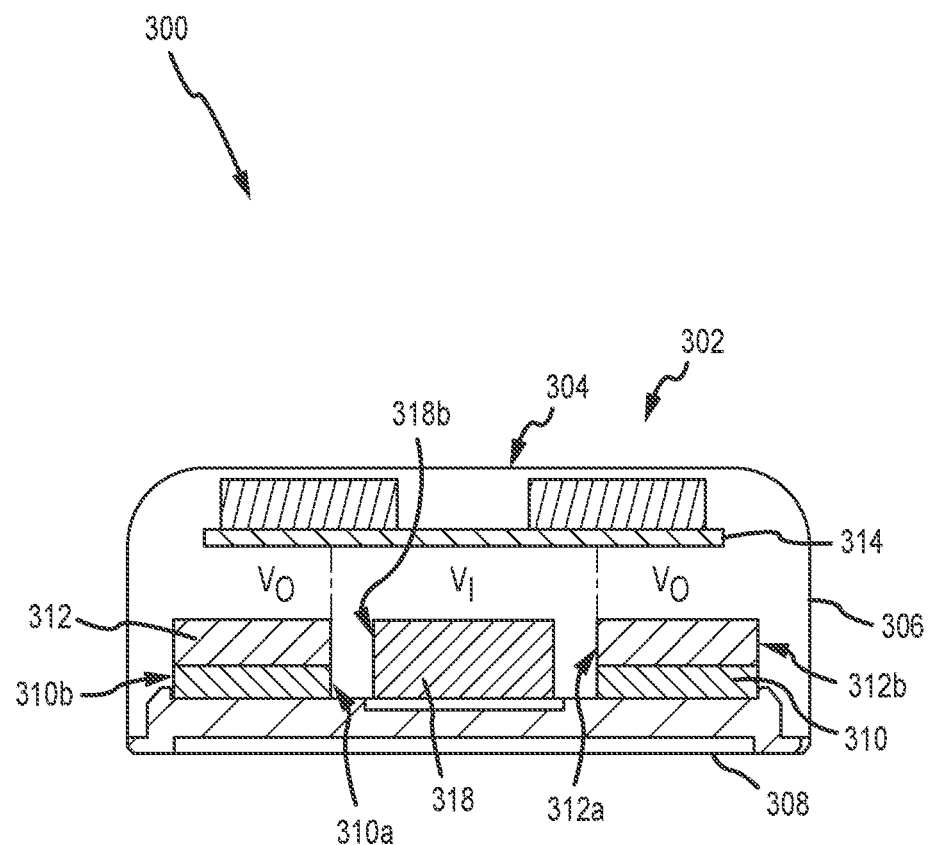
FIG. 4 is a side sectional view of the external portion of FIG. 3.

FIG. 3 is an exploded perspective view of an external portion 300 of an auditory prosthesis, while FIG. 4 depicts a side sectional view of the external portion 300. These two figures are described simultaneously. The external portion 300 includes a body 302 that includes an upper wall 304 and an outer wall 306. A base 308 defines the lower extent of the external portion 300 and together with the body 302 defines a body or housing volume V, in which the various components are contained. In embodiments, the housing volume V can be further parsed into two discrete volumes, an outer volume $V_O$ and an inner volume $V_I$. The outer volume $V_O$, in the depicted embodiment, contains an external coil 310 and a shield 312 disposed above (relative to the base 308) the external coil 310. Each of the external coil 310 and a shield 312 are annular in shape. The outer volume $V_O$ is defined by an inner coil edge 310a. In other embodiments, the outer volume $V_O$ is defined by an inner shield edge 312a. In certain embodiments, the outer volume $V_O$ can be defined by an outer coil edge 310b or an outer shield edge 312b. In other embodiments, the outer volume $V_O$ can be at least partially defined by the outer wall 306. A substrate 314 that supports the various speech processing components 316 and the base 308 further define the upper limits of the outer volume $V_O$. Thus, the space defined by the substrate 314, the base 308, the inner coil edge 310a, and either of the outer coil edge 310b and the outer wall 306 defines the outer volume $V_O$ and contains the coil 310 and shield 312. The inner coil edge 310a and the inner shield edge 312a, along with the substrate 314 and the base 308, also define the inner volume $V_I$. The inner volume $V_I$ contains a magnet 318 that, in certain embodiments, is cylindrical in shape and has an outer magnet edge 318b.

In certain embodiments, the coil 310 and shield 312 are arranged and sized so as to be aligned. For example, the inner coil edge 310a can be aligned with the inner shield edge 312a. Similarly, the outer coil edge 310b can be aligned with the outer shield edge 312b. The outer magnet edge 318b is smaller than the inner coil edge 310a, so that the magnet 318 is completely disposed within the space defined by the inner coil edge 310a. Center points of each of the coil 310, the shield 312, and the magnet 318 can be aligned along an axis A that is substantially orthogonal to both the base 308 and the substrate 314. The cross sectional shapes (e.g., parallel to the base 308) of each of the outer volume $V_O$ and the inner volume $V_I$ can be defined by the shape of the coil 310 and shield 312. The depicted coil 310 and shield 312 are circular in shape to maximize the coupling of magnetic flux produced by the external coil 310 and the associated implanted coil (not shown). Other coil 310 and/or shield 312 shapes, such as substantially circular, oval, substantially oval, and D-shaped, can be used. The depicted circular shape at least partially defines an outer volume $V_O$ having a substantially annular cross section, along with an inner volume $V_I$ having a substantially cylindrical cross section.

The outer volume $V_O$ and inner volume $V_I$ are characterized by differences in magnetic permeability. Each of the coil 310 and the magnet 318 generate a magnetic flux. The magnetic permeability of the outer volume $V_O$ is based at least in part on the presence of the shield 312, which substantially redirects the magnetic flux generated by the coil 310 and therefore, has a higher magnetic permeability than the inner volume $V_I$. The magnetic permeability of the inner volume $V_I$ is based at least in part on the absence of any material that substantially redirects the magnetic flux generated by the magnet 318. In certain embodiments, the magnet 318 is separated from the inner shield edge 312a by a gap of gas. This gas can be air, which has a magnetic permeability less that the material utilized in the shield 312. Thus, the inner volume $V_I$ contains only the magnet 318. In other embodiments, the magnet 318 is separated from the inner coil edge 310a by a gap of air, but a portion of the shield 312 can be disposed in the inner volume $V_I$, such that the inner volume $V_I$ contains only the magnet 318 and a portion of the shield 312. In other embodiments, the inner volume $V_I$ contains a foam or other flexible or semi-flexible material that defines spaces for receiving the gas. The foam can serve as an insulating or cushioning material. In general, the magnetic flux permeability of any material dispersed in the inner volume $V_I$ will be less than that of the shield material, but slightly greater than the gas. Regardless, one characteristic of the present aspects disclosed herein is the absence of any material proximate the magnet (e.g., above the magnet 318) to alter or redirect the magnetic flux thereof.

Many prior art medical devices, such as cochlear implants and other auditory prostheses, utilize a shield material between an electronics module and one or more internal components that generate magnetic flux, for example, magnets, coils, etc. Magnetic flux can interfere with the operation of the electronics module. Additionally, having magnetic flux passing through the electronics module can limit effectiveness or efficiency of RF links between mating or matching coils (e.g., between external coils and implanted coils). If the inner diameter of this shield material is small, the tuned frequency of the external coil can be unacceptably sensitive to changes in magnet strength. Recipients of a cochlear implant system have the option to select a magnet having a desired strength to provide sufficient retention and comfort. The ability to change weaker magnets for stronger magnets can be desirable due to the variability of recipient skin flap thickness after surgery. That is, thicker skin flaps can necessitate stronger magnets. With this small inner diameter shield, tuning ranges of 300 kHz are observed from the weakest to the strongest magnet strength. This deviation from the nominal selected tuned frequency means that recipients with stronger and weaker magnets will suffer from a less efficient and less effective RF link.

Increasing the inner diameter of the shield material in this manner can be effective in reducing the change in tuned frequency due to the change in magnet configuration. This can result in a 60 kHz tuning range from the weakest magnet configuration to the strongest, which means recipients with stronger and weaker magnets can experience a more effective and efficient RF link. This maximizes retention magnet options for recipients while preserving intended RF link performance. The aspects disclosed herein also reduce need for retention magnet repositioning, with attendant thickness increase implications.

Figure 5A:
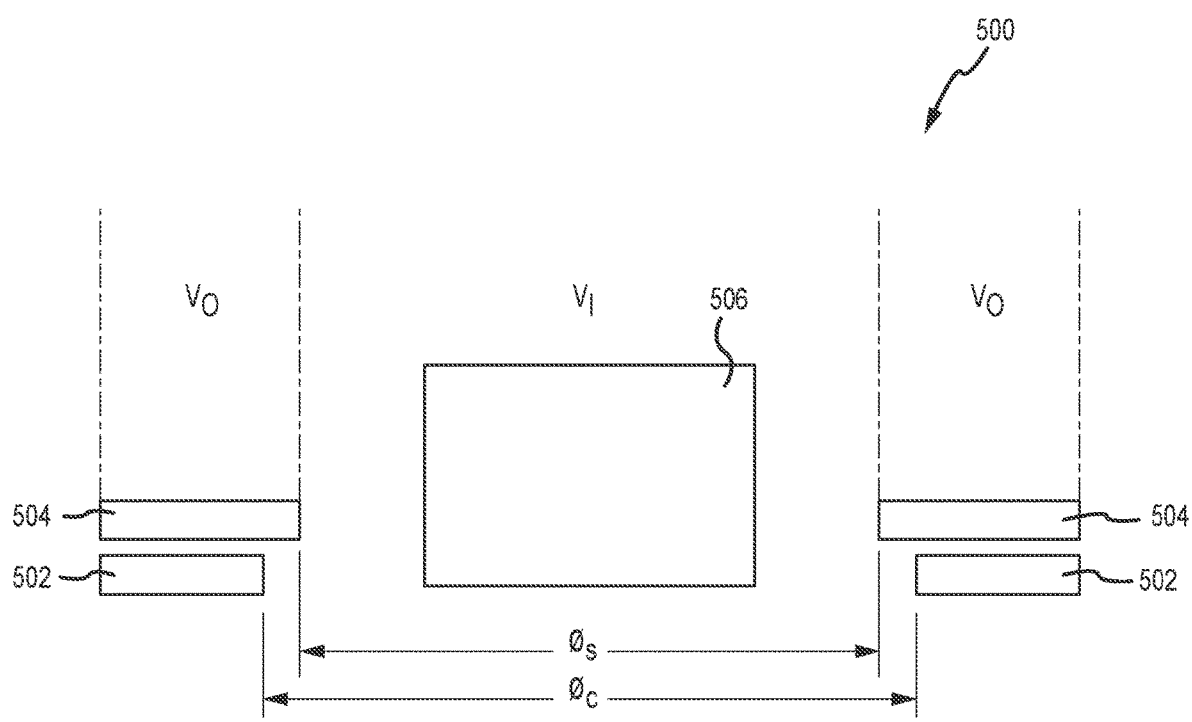
FIG. 5A depicts a test model of an external portion of an auditory prosthesis.

Testing has confirmed that an absence of shielding material in the inner volume $V_I$ of an external portion of a cochlear implant configured as described herein significantly decreases the change in tuned frequency experienced by the external coil. FIG. 5A depicts a test model of an external portion 500 of a cochlear implant, shown in section. Here, the external portion 500 test model includes an external coil 502 with a shield 504 disposed above the coil 502. A magnet 506 is disposed within an inner volume $V_I$ defined by a shield inner diameter ØS of the shield 504. In general, the shield inner diameter ØS is smaller than the coil inner diameter $Ø_C$. FIG. 5B depicts the effect on frequency range for a shield having various shield inner diameters $Ø_S$. No magnetic shielding material (such as above or around the magnet 506) was otherwise disposed in the inner volume $V_I$. Interestingly, coil tuned frequency range decreases as the shield inner diameter $Ø_S$ increases. Thus, an external portion of an auditory prosthesis having a shield inner diameter $Ø_S$ substantially equal to a coil inner diameter $Ø_C$ would likely have the lowest tuned frequency range.

These results are particularly compelling for coils used in the external portions of auditory prostheses that are configured to utilize a plurality of replaceable magnets having varying strengths. For example, as described above, in a cochlear implant auditory prosthesis, an external portion is located and retained on the head, proximate an implanted portion. Typically, this retention is due to the utilization of magnets, one in the external portion, and one in the implanted portion. The thickness of a skin flap between the external portion and the implanted portion can vary significantly depending on implant depth, skin thickness, or other factors. This often requires the use of magnets having different strengths, with magnets having the strongest strengths being used, for example, due to thicker skin flaps. Thus, a single external processor can be used with a number of magnets having different retention strengths. With reference to FIG. 5A, changing the strength of the retention magnet 506 in the external portion 500 changes the amount of retention magnetic flux that permeates the shield material 504 disposed above the coil 502, which in turn changes the inductance of the coil 502 and thereby changes its tuned frequency. The tuned frequency has a significant impact on the effectiveness and efficiency of the coil 502.

The results in the graph depicted in FIG. 5B indicate that increasing the inner diameter $Ø_S$ of the shield 504, such that shielding material is disposed further away from the magnet 506, significantly decreases the change in tuned frequency experienced by the coil 502 with changing retention magnet strength. In an embodiment, increasing the shield inner diameter $Ø_S$ so as to be substantially equal to the coil inner diameter $Ø_C$, distances the shield 504 as far from the magnet 506 as possible, while still providing the shield 504 between the coil 502 and the electronics disposed in the external portion 500, above the coil 502. This decreases the impact of changing retention magnet strength on coil effectiveness and efficiency.

Figure 6A:
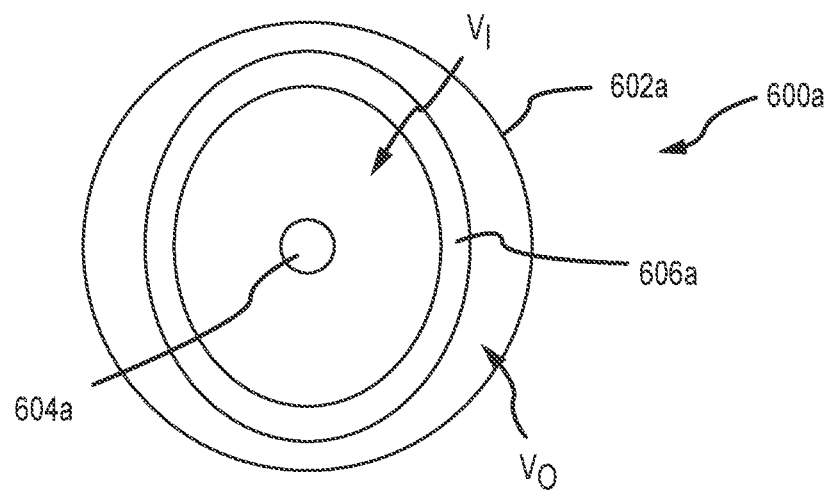
FIGS. 6A-6B depict top section views of alternative coil shapes for coils utilized in external portions of auditory prostheses.
Figure 6B:
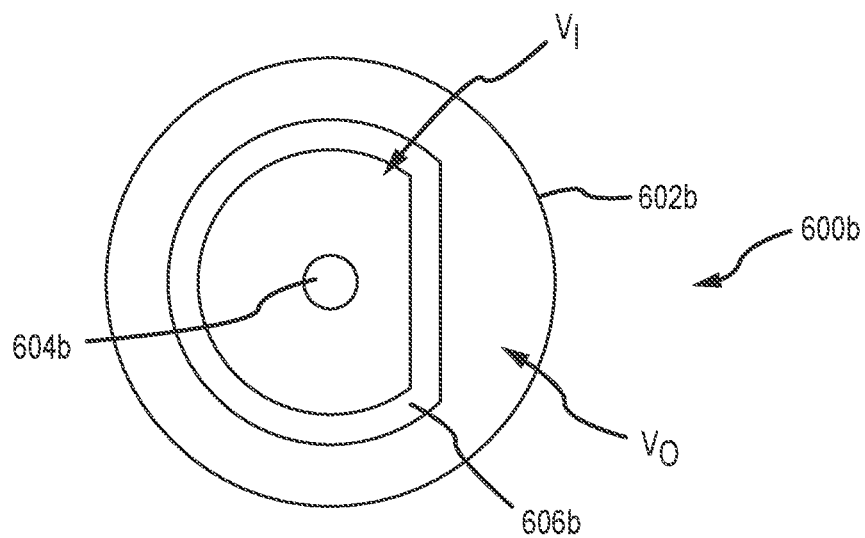

FIGS. 6A-6B depict top section views of alternative coil shapes for coils utilized in external portions of auditory prostheses. Two external portions 600a, 600b are depicted. In FIG. 6A, the external portion 600a includes an outer housing 602a and a magnet 604a disposed therein. A coil 606a having an oval shape is also depicted. Thus, the inner volume $V_I$ is defined at least in part by an inner edge of the coil 606a and thus has a generally cylindrical volume having an oval cross-sectional shape. As described herein, an outer volume $V_O$ is defined by the inner edge of the coil 606a and either an outer edge of the coil 606a or the housing 602a. In FIG. 6B, the external portion 600b includes an outer housing 602b and a magnet 604b disposed therein. A coil 606b having a substantially D-shape is also depicted. Thus, the inner volume $V_I$ is defined at least in part by an inner edge of the coil 606b and thus has a generally cylindrical volume having a D-shaped cross-sectional. As described herein, an outer volume $V_O$ is defined by the inner edge of the coil 606a and either an outer edge of the coil 606b or the housing 602b. In other aspects, inner and/or outer edges of coils and shields can be substantially round or substantially oval.

This disclosure described some embodiments of the aspects disclosed herein with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific aspects were described herein, the scope of the disclosed embodiments are not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An apparatus comprising:
a coil comprising an inner coil diameter;
a substantially annular shield comprising an inner shield diameter, wherein the substantially annular shield comprises a first magnetic flux permeability, and wherein the inner coil diameter and the inner shield diameter at least partially define a volume;
a magnet at least partially disposed within the volume; and
a gas disposed within the volume, wherein the gas comprises a second magnetic flux permeability less than the first magnetic flux permeability.

2. The apparatus of claim 1, wherein the gas comprises air.

3. The apparatus of claim 1, wherein the gas is contained within a material comprising a third magnetic flux permeability less than the first magnetic flux permeability.

4. The apparatus of claim 1, wherein the magnet comprises a magnet center point, wherein the magnet center point is substantially aligned with a coil center point of the coil and a shield center point of the substantially annular shield.

5. The apparatus of claim 1, wherein the magnet comprises an outer magnet diameter less than the inner coil diameter and the inner shield diameter, such that a gap is defined between the magnet and the substantially annular shield.

6. The apparatus of claim 1, wherein the coil comprises an outer coil diameter and the substantially annular shield comprises an outer shield diameter, wherein the outer coil diameter and the outer shield diameter are substantially aligned.

7. The apparatus of claim 1, further comprising a substrate disposed above the magnet, wherein the substrate at least partially defines the volume, and wherein the volume has magnetic flux permeability less than the first magnetic flux permeability.

8. The apparatus of claim 1, wherein the apparatus further comprises a base and the coil is disposed between the substantially annular shield and the base.

9. An apparatus comprising:
an outer volume having a first magnetic flux permeability, wherein the outer volume contains:
a coil comprising an inner coil diameter;
a shield substantially aligned with and disposed above the coil, wherein the shield comprises an inner shield diameter, and wherein the first magnetic flux permeability is at least partially defined by the shield; and
an inner volume having a second magnetic flux permeability less than the first magnetic flux permeability, wherein the inner volume is at least partially defined by the inner coil diameter and the inner shield diameter, and wherein the inner volume contains a magnet.

10. The apparatus of claim 9, wherein a center point of each of the coil, the shield, and the magnet are aligned with an axis.

11. The apparatus of claim 9, wherein the coil and the shield are outside of the inner volume.

12. The apparatus of claim 9, wherein the coil comprises an outer coil diameter and the shield comprises an outer shield diameter substantially aligned with the outer coil diameter, and wherein the outer volume is at least partially defined by the outer coil diameter and the outer shield diameter.

13. The apparatus of claim 12, wherein the outer volume is substantially annular, and wherein the inner volume is substantially cylindrical.

14. The apparatus of claim 13, wherein the inner volume includes a gas having a magnetic flux permeability that is less than the first magnetic flux permeability.

15. The apparatus of claim 13, wherein the inner volume includes a foam material having a magnetic flux permeability that is less than the first magnetic flux permeability.

16. An apparatus comprising: a coil comprising an inner coil diameter;
a shield comprising an inner shield diameter, wherein the inner coil diameter and the inner shield diameter at least partially define a volume, wherein the shield is configured to redirect a magnetic flux generated by the coil; and
a magnet at least partially disposed within the volume.

17. The apparatus of claim 16, further comprising a substrate disposed above the shield, wherein the substrate at least partially defines the volume.

18. The apparatus of claim 16, further comprising a base disposed below the coil, wherein the base at least partially defines the volume.

19. The apparatus of claim 16, wherein the coil comprises a shape that is at least one of round, substantially round, oval, substantially oval, and D-shaped.

20. The apparatus of claim 19, wherein the volume is substantially cylindrical.

* * * * *